United States Patent [19]

Onwumere et al.

[11] Patent Number: 5,159,051

[45] Date of Patent: * Oct. 27, 1992

[54] BIOSTABLE POLYURETHANE

[75] Inventors: Fidelis C. Onwumere, Woodbury, Minn.; Nancy L. Shields, Dayton, Ohio

[73] Assignee: Becton, Dickinson and Company, Franklin Lakes, N.J.

[*] Notice: The portion of the term of this patent subsequent to Oct. 27, 2009 has been disclaimed.

[21] Appl. No.: 697,848

[22] Filed: May 9, 1991

[51] Int. Cl.$^5$ .............. C08G 18/70; C08B 37/10; A61K 31/725; A61K 31/765

[52] U.S. Cl. .................. 528/67; 424/78.08; 514/56; 536/21; 428/36.9; 428/364; 428/398

[58] Field of Search .......... 528/67; 424/78.08; 514/56; 536/21; 428/36.9, 364, 398

[56] References Cited

U.S. PATENT DOCUMENTS

| | | | |
|---|---|---|---|
| 3,634,123 | 1/1972 | Eriksson | 428/447 |
| 3,766,104 | 10/1973 | Bonin | 528/80 |
| 3,810,781 | 5/1974 | Eriksson et al. | 424/423 |
| 3,969,301 | 7/1976 | Thurn | 528/67 |
| 4,024,871 | 5/1977 | Stephenson | 424/443 |
| 4,349,467 | 9/1982 | Williams et al. | 523/112 |
| 4,521,564 | 6/1985 | Solomon et al. | 523/112 |
| 4,613,517 | 9/1986 | Williams et al. | 424/78.18 |
| 4,865,870 | 9/1989 | Hu et al. | 427/2 |
| 4,873,308 | 10/1989 | Coury et al. | 528/75 |
| 4,978,691 | 12/1990 | Murai et al. | 521/172 |

OTHER PUBLICATIONS

Lemm, *Polyurethanes in Biomedical Engineering*, H. Planck et al., ed., Elsevier Science Publishers, Amsterdam, The Netherlands, 1984, p. 103.
*Biomaterials*, 218, 1983, Ferruti et al.
Azzuoli et al., *Biomaterials*, 8, 61, 1987.
Smith et al., *Anal. Biochem.*, 109, 466, 1980.
Brown, *Hematology Principles and Procedueres*, Third Edition, Lea and Febiger Co., 1980.

*Primary Examiner*—John Kight, III
*Assistant Examiner*—Rabon Sergent
*Attorney, Agent, or Firm*—Richard E. Brown

[57] ABSTRACT

A thermoplastic polyurethane having prolonged biostability has tertiary amino groups in the polymer chain. Protonation of the amino groups with an aqueous acid causes the polymer to absorb up to 1,700% by weight of water and swell. The protonated amino groups form a complex with an antithrombogenic agent to give an antithrombogenic polyurethane. The invention includes a shaped article of the polyurethane.

20 Claims, No Drawings

BIOSTABLE POLYURETHANE

BACKGROUND OF THE INVENTION

1. Field of the Invention

This invention relates to biomedical devices, and more particularly relates to a polyurethane of high stability to body fluids which are suitable for long term implants.

2. Background of the Invention

Extensive investigations have been undertaken over many years to find materials that will be biologically and chemically stable toward body fluids. This area of research has become increasingly important with the development of various objects and articles which can be in contact with blood or other body fluids, such as artificial organs, vascular grafts, probes, cannulas, catheters and the like. Biostability is particularly important for articles intended for long term contact with the body environment.

Synthetic plastics are preferred materials for such articles. Polyurethanes in particular possess an outstanding balance of physical and mechanical properties and superior blood compatibility compared to other polymers such as silicone rubber, polyethylene, polyvinyl chloride and perfluorinated polymers. As a result, they have come to the fore as the preferred polymeric biomaterials for fabrication of various medical device components. Some important device applications for polyurethanes include peripheral and central venous catheters, coatings for heart pacemaker leads and the Jarvik heart.

Polyurethanes are synthesized from three basic components, a polyisocyanate, a polyglycol and an extender, usually a low molecular weight diol, diamine, aminoalcohol or water. If the extender is a diol, the polyurethane consists entirely of urethane linkages. If the extender is water, aminoalcohol or a diamine, both urethane and urea linkages are present and the polyurethane is more accurately and conventionally termed a polyurethaneurea. In the present disclosure, polyurethanes and polyurethaneureas are generically referred to as polyurethanes.

Polyurethanes are known to develop microdomains conventionally termed hard segments and soft segments, and as a result are often referred to as segmented polyurethanes. The hard segments form by localization of the portions of the polymer molecules which include the isocyanate and extender components and are generally of high crystallinity. The soft segments form from the polyglycol portions of the polymer chains and generally are either noncrystalline or of low crystallinity. Crystallinity and hard segment content are important contributing factors to polymer properties. A discussion of the effect of structure on the stability of polyurethanes has been presented by Lemm in *Polyurethanes in Biomedical Engineering*, H. Planck et al., ed., Elsevier Science Publishers, Amsterdam, The Netherlands, 1984, p 103.

The usual polyglycols for polyurethane synthesis are polyetherglycols and polyester lycols. It is, however, well-known that both of these classes of polyglycol soft segment components are subject to degradation in the body environment and may not be suitable for biomedical applications. On one hand, segmented polyurethanes produced from polyester diol soft segments may be subject to rapid hydrolysis of the ester functional group. On the other hand, polyurethanes produced with polyether diol soft segment have been reported to undergo extensive oxidative degradation. It is therefore desirable to eliminate these functional groups during the initial design of a potentially biostable polyurethane, and various disclosures have been directed to polyurethanes having other soft segments. Thus, Coury et al., in U.S. Pat. No. 4,873,308 discloses polyurethanes in which the soft segment is a hydrocarbon diol. Likewise, Murai et al., in U.S. Pat. No. 4,978,691 discloses polyurethanes in which the soft segment is a polycarbonate diol.

A second problem with respect to use of polymers for biomedical devices is the thrombogenic potential of polymeric surfaces in contact with blood. Thrombogenicity has conventionally been counteracted by the use of anticoagulents such as heparin. Various procedures for attachment of heparin to otherwise thrombogenic surfaces have been disclosed. Eriksson et al., in U.S. Pat. No. 3,634,123 discloses steeping a plastic surface sequentially in a solution of a cationic surface active agent and an aqueous solution of heparin to ionically bond the heparin. Improvements in the surface active agent method have been disclosed by Eriksson in U.S. Pat. No. 3,810,781, by Williams et al. in U.S. Pat. Nos. 4,349,467 and 4,613,517 and by Hu et al. in U.S. Pat. No. 4,865,870.

Ferruti et al. disclose the heparin binding capacity of crosslinked polyamidoamines prepared by reacting diamines with bis acryloylpiperazines (*Biomaterials*, 218 (1983). Azzuoli et al., in *Biomaterials* 8,61 (1987) coats a polyurethane with a diisocyanate, and reacts the diisocyanate with the polyamidoamine of Ferruti et al. supra. The grafted polyamidoamine is then protonated and treated with a heparin salt.

Covalent bonding of aldehyde-actuated heparin to an amine rich polyurethane surface is disclosed by Solomon et al. in U.S. Pat. No. 4,521,564.

While the above disclosures have improved materials for biomedical devices, further improvements, in particular long term stability are needed. The present invention is directed to fulfilling this need.

SUMMARY OF THE INVENTION

A thermoplastic substantially hydrophobic polyurethane having latent hydrophilicity has tertiary amino groups in the polymer chain. Preferred polyurethanes include an aromatic diisocyanate an alicyclic diisocyanate, and a diol chain extender in the hard segment. The soft segment includes a hydroxy-terminated polyurethane prepolymer. The prepolymer is preferably the reaction product of an aliphatic diisocyanate and a dihydroxy tertiary amine. The polyurethane is substantially hydrophobic, but when contacted with an aqueous acid, the amino groups are protonated and the polymer becomes hydrophilic, absorbs up to 1,700% by weight of water, and undergoes substantial swelling.

Another aspect of the invention is a polyurethane which is antithrombogenic, thermoplastic and hydrophilic. The antithrombogenic polyurethane is prepared by steeping the substantially hydrophobic polyurethane in a dilute aqueous acid solution containing an antithrombogenic agent, preferably heparin, whereby an ionic complex forms between the antithrombogenic agent and the protonated amino group.

The polyurethane, in either its hydrophobic or hydrophilic state, may be supplied as a shaped medical article, such as a swellable or nonswellable catheter.

Preferred medical articles are antithrombogenic catheter tubings and obturator rods.

The polyurethane of this invention when protonated expands six to ten times more than swellable polyurethanes made with conventional hydrophilic soft segments such as polyethylene glycol, and the rate of water or saline uptake is much faster. The tertiary amine pendent group along the polymer chain can be used to ionically attach bioactive agents, such as anti-infective/antithrombogenic agents or antibiotics without the use of conventional quaternary ammonium salt complexing agent. Unlike expandable polyurethanes formed from hydrophilic polyols, the polyurethane of this invention can be used in the unhydrated state as a nonswellable medical article or if desired, it can be hydrated and used as an expandable article.

The heparinized article of the invention does not include a coating of quaternary salt on a preformed device because the complexing agent is an integral part of the polymer chain. Thus, there is no danger of separation of quaternary salt into a patient's blood stream. Since quaternary salts are known to be hemolytic, an added margin of patient safety is provided by the present invention.

Release of heparin from the heparinized catheter of the invention is almost undetectable after a few hours in contact with normal saline, yet the heparinized surface remains antithrombogenic after 10 days. For patients on long term heparin therapy, this represents another safety factor because of the recently recognized and difficult to diagnose condition known as heparin-induced thrombocytopenia.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the invention, the new polyurethane is hydrophobic and has excellent physical properties making it useful for any application where water absorption is not desired. On the other hand, it has latent hydrophilicity so that the same material may be used for applications where it is desirable to combine its favorable mechanical properties with softness and swelling resulting from water absorption.

The polyurethane of the invention may be prepared, as described below, from three essential components. The first component of the new polyurethane is hereinafter called the isocyanate fraction. This fraction contains at least an aromatic diisocyanate and a nonaromatic diisocyanate. Suitable aromatic diisocyanates are toluene diisocyanate, 3,3'-diphenylmethane diisocyanate, 1,4-phenylenediisocyanate, 2,2'-dimethyl-4,4'-biphenyldiisocyanate and 3,3'-dimethyl-4,4'-biphenyldiisocyanate. The preferred aromatic diisocyanate is 4,4'-diphenylmethanediisocyanate (MDI).

The nonaromatic diisocyanate may be any aliphatic or alicyclic diisocyanate as known in the polyurethane art. Suitable nonaromatic diisocyanates have from about 4 to 18 carbon atoms and may be branched or straight chain. Representation of such diisocyanates are 1,12-dodecanediisocyanate, 1,11-undecanediisocyanate, 1,10-decanediisocyanate, 1,9-nonanediisocyanate, 1,8-octanediisocyanate, 1,7-heptanediisocyanate, trimethyl-1,6-hexanediisocyanate, 1,4-cyclohexanediisocyanate, 4,4'-dicyclohexylmethyldiisocyanate and preferably 1,6-hexanediisocyanate (HDI). The disclosure will hereinafter be described in terms of the preferred MDI and HDI. The ratio of MDI and HDI in the isocyanate fraction may be about 35:65 to 65:35, preferably about 50:50 mole percent.

The second component of the new polyurethane is a chain extender. Suitable chain extenders may be low molecular weight branched or unbranched diol, diamine or aminoalcohol of up to 10 carbon atoms, optionally fluorinated, or mixtures thereof. Representative nonlimiting examples of chain extenders are ethylene glycol; diethylene glycol; triethylene glycol; 1,2-propanediol; 1,3-propanediol; 1,6-hexanediol; 1,4-hydroxymethyl cyclohexane, hydroquinone dihydroxyethyl ether, ethanolamine, ethylenediamine, bis hydroxyethylpiperazine and hexamethylenediamine. Preferred chain extenders are 1,6-hexanediol, ethylenediamine, and hexamethylenediamine, most preferably, 1,4-butanediol (BDO).

The third component of the new polyurethane is an all aliphatic, tertiary amine-containing hydroxy-terminated polyurethane prepolymer which serves as a nonether, nonester soft segment. This component may be the reaction product of about one mole of an aliphatic diisocyanate and about 1.5 moles of a bis (hydroxyalkyl) tertiary amine. Any aliphatic diisocyanate as described above for the isocyanate fraction may be used for synthesis of the prepolymer, preferably HDI and trimethyl-1,6-hexane diisocyanate.

Bis (hydroxyalkyl) tertiary amines which may be used for prepolymer synthesis may have structure (1) below.

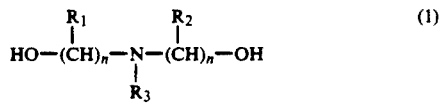

In structure (1), $R_1$ and $R_2$ may independently be hydrogen or lower alkyl, $R_3$ may be lower alkyl or dialkylaminoalkylene, and n may be 2 to 6. In structure (1), the term alkyl means about 1 to 18 carbon atoms and the term alkylene means about 2 to 6 carbon atoms. Suitable tertiary amines are, for example, N-methyldiethanolamine, N-dodecyldiethanolamine, N-octadecyldiethanolamine, N-ethyldiisopropanolamine, dimethylaminopropyldiisopropanolamine, and diethylaminopropyldipropanolamine. The preferred bis (hydroxyalkyl) tertiary amine is N-butyldiethanolamine (BDA). This product is available from Union Carbide Corporation, (Bound Brook, N.J.) and the invention will henceforth be described in terms of the preferred BDA.

The polyurethane of the invention may be synthesized by any conventional procedure as known in the polyurethane art. Preferably, a modification of the standard one shot method may be used in which the components of the prepolymer are mixed and stirred rapidly until the exotherm subsides and all isocyanate groups have reacted with hydroxyl groups. In this reaction, the tertiary amino group of the BDA serves as a catalyst for the prepolymer formation. The isocyanate fraction and the chain extender may then be added, either as a mixture or, preferably, sequentially with the extender added and mixed with the prepolymer followed by the isocyanate fraction. Example I describes a typical synthetic procedure. As described above, the basic amino groups of the DPA catalyze the reaction of the isocyanate fraction with the hydroxyl groups of the prepolymer and extender.

The hard segment (HS) content of the new polyurethane may be about 30 to 70, preferably 45-60, most preferably about 50%. In this disclosure, the HS is calculated on the basis of the isocyanate fraction and extender and does not include the diisocyanate component of the prepolymer since this ingredient reacts only with the BDA and not with the extender. An isocyanate index of 1.0 to 1.1, preferably 1.02 may be used. From the desired HS content of the product, the isocyanate index and the molecular weights of the components, the proportions of the reagents to be used may readily be calculated.

If desired, the polyurethane may be crosslinked by inclusion in the formulation of a conventional polyurethane crosslinker, such as trimethanolpropane. The preferred polyurethane does not contain any crosslinkers and accordingly is fully thermoplastic and may be melt processed by extrusion or molding operations into any desired shape, such as rods, ribbons, tubings and sheets. Example II describes a typical melt processing experiment.

It has been found that the polyurethane of the invention is substantially hydrophobic, i.e., water absorption at equilibrium (after 6 hours soaking) is less than about 5%. These polymers have excellent mechanical properties and may find utility in a variety of applications for which water absorption is not useful.

On the other hand, if the polymer of the invention is hydrated in acidified water, it absorbs water up to 1,700% of its original weight. Hydration is accompanied by swelling and softening and may be performed in any dilute acid, preferably, an organic acid. The most preferred acid for hydration may be dilute acetic acid of about 1 to 5, preferably about 3% by volume. Hydration is substantially complete after 1 hour at 50° C. or about 8 hours at ambient temperature.

Advantage may be taken of the ability of the polyurethane to absorb water to prepare an anti-infective or antithrombogenic medical device. In this aspect of the invention, a medical device such as a rod to be used as an obturator or a tubing to be used as a catheter, may be melt processed into the desired shape and the shaped article steeped with acidified water, as described in Example III. The amino groups in the polyurethane chains are thereby protonated. When the amino groups are protonated, the hydrophobic polyurethane becomes hydrophilic and water absorption takes place. If the acidified water contains a bioactive agent capable of complexing with the protonated nitrogen atom, a polyurethane having the bioactive agent complexed to the nitrogen atom of the polymer chain is formed. No intermediate coating layer is required. Suitable bioactive agents are anti-infective agents, and antithrombogenic agents containing carboxyl and sulfonate groups capable of complexing with the protonated amine. Suitable anti-infective agents are antibiotics such as penicillin and suitable antithrombogenic agents may be prostaglandins, urokinase, streptokinase tissue plasminogen activator and heparinoids. The preferred agent is heparin wherein protonation, hydration and heparinization are performed simultaneously by steeping the polyurethane in about a 0.05% by weight solution of sodium heparinate in 3% acetic acid. During the water absorption, the heparin is carried into the polyurethane so that the complexation of heparin occurs throughout the polymer matrix rather than just on the surface as in prior art methods. Example IV describes the heparinization procedure.

The following examples are provided to further illustrate the invention but are not to be considered as limitative of the invention.

EXAMPLE I

A. Prepolymer Synthesis

A 5 liter glass reactor equipped with mechanical stirrer, thermometer and a nitrogen gas inlet was charged with 2.4 kg (15 moles) of N-butyldiethanolamine. While stirring, 2.1 kg (5 moles) of trimethyl-1,6-hexanediisocyanate was added to the reactor. Heat was not applied because the reaction was highly exothermic. The reaction was complete (disappearance of isocyanate by Infra Red) in about 4 hours.

B. Synthesis of 30% HS Polyurethane

Into a metal can was added 840 g of the hydroxy-terminated prepolymer from A and 49 g of BDO. With high speed air stirrer, the components were mixed thoroughly. To the can was added a mixture of 166 g of MDI and 145 of HDI. The whole mixture was stirred for about 2 minutes or until an exotherm of 100° C. was reached. The clear viscous melt was immediately poured into a teflon sheet and cured in an oven at 125° C. for one hour.

EXAMPLE II

Melt Processing

The polyurethanes from Example I were pelletized a twin screw extruder, and the pellets then extruded into rods, ribbons and tubings using a 1 inch extruder.

EXAMPLE III

Polyurethane Water Absorption

Using a 30% HS polyurethane rod of 0.16 cm diameter, water absorption and increase of outside diameter (O.D.) were determined by steeping measured lengths of the rods in a 3% aqueous solution of acetic acid at 40° C. and withdrawing the rods periodically to measure weight differences and O.D. The results obtained are given in Table I:

TABLE I

| INDWELLING TIME (min) | % WEIGHT INCREASE | % INCREASE IN O.D. |
|---|---|---|
| 5 | 64 | 29 |
| 10 | 90 | 45 |
| 25 | 245 | 88 |
| 45 | 486 | 134 |
| 60 | 667 | 179 |
| 120 | 1684 | |
| 240 | 1688 | |

EXAMPLE IV

A. Heparinization of 30% HS Rod

The hydrated 50% HS rod of Example III was dehydrated in a forced air oven at 50° C. for 1 hour. A heparin solution was made by dissolving 0.5 g of sodium heparinate in 100 ml of distilled water. To this solution was added 3 ml of glacial acetic acid. About 125 sq cm of rod were steeped in the acidified heparin solution at 40° C. for 2 hours, then rinsed to remove occluded heparin solution from the rod surface.

The heparinized rod was again dehydrated and rehydrated by steeping in normal saline until an equilibrium weight was obtained. This experiment showing hydration and dehydration of an extruded rod illustrates the preferred sequence of steps for fabrication of the catheter or obturator of the invention ready for rehydration and heparinization in 3% acetic acid.

EXAMPLE V

Antithrombogenicity—In vitro

The heparin incorporated into the polyurethane rods was determined by three test protocols after rinsing the heparinized rods for 4,8 and 24 hours and 10 days in normal saline. Release rates and total extractable heparin were assayed colorimetrically using toluidine blue, as described by P. K. Smith, et al., "Colorimetric method for the assay of heparin content in immobilized heparin preparations," Anal. Biochem., 109, 466 (1980). In vitro heparin actively was determined by the partial thromboplastin time (P.T.T., a measure of the clotting time) as described by B. A. Brown, *Hematology Principles and Procedures*, Third Edition, Lea and Febiger Co. 1980. Heparin activity on the surface of the rod was determined using the Thrombin Inactivation Assay, (Chandler et al., *J. Biomedical Materials Research*, 22, 497 (1988).

The results of these experiments are given in Table II:

TABLE II

| TIME (hours) | TOTAL HEPARIN QUANTITY EXTRACTED 81 ug/cm$^2$ | | |
|---|---|---|---|
| | RELEASE RATE (ug/cm$^2$/min) | P.T.T. (secs) | SURFACE ACTIVITY (units/cm$^2$) |
| 0 | | >1800 | |
| 1 | | >1800 | |
| 4 | 0.075 | >1800 | 0.026 |
| 8 | 0.007 | >1800 | 0.036 |
| 24 | <test range | >1800 | 0.031 |
| 10 days | <test range | >1800 | 0.066 |

Release rate and surface activity were not performed on the 0 and 1 hour intervals because a significant portion of the heparin release at these intervals is due to adsorbed heparin rinsing out of the system and has a negligible effect on the long term performance of the system. It is seen that the P.T.T. and surface activity tests demonstrate that heparin activity is still present long after the release rate study shows that heparin release is complete.

EXAMPLE VI

Long Term Implantation Study

A. Sample Order and Placement

This implant study was conducted on a control rod of a commercially available polyether polyurethane and a test rod of the polyurethane of Example I. In addition, a 16 gauge tubing of the control polyurethane and a 16 gauge tubing having layers of the polyurethane of Example I laminated onto both the lumen and outside surfaces of the control polyurethane were studied.

The test intervals selected for this study were 2 weeks, 4 weeks, 8 weeks and 12 weeks. For each interval, 9 rabbits were used to implant rod samples with 6 implant locations per rabbit. The sample locations in each rabbit were determined using a statistical randomization scheme. Each sample was coded with its corresponding rabbit identification number and implantation location site code.

B. Rod Implantation for Tensile Studies

Each animal was anesthetized using an intramuscular dose of ketamine and rompum (1:1 ratio) at 1 mg/kg body weight. The hair was clipped from the back of the rabbit from the shoulders to the haunches. The clipped area was swabbed with isopropyl alcohol followed by 3% betadine solution. The animal was then transferred to a sterile surgical table and the back of the rabbit covered with a sterile fenestrated surgical drape. Aseptic techniques were used during the implantation of the samples. A #20 scalpel was used to make a 5 inch incision through the skin over the spinal cord on top of the latissimus dorsi and paravertebral muscles. The skin incision site was moved over the implant site (approximately ½ inch lateral to the spinal column. A 1 cm incision was made in the fascia connecting the latissimus dorsi to the spinal column. A pocket was made between the muscle and fascia using a hemostat, and a test sample was placed in the pocket. A total of six samples were implanted in the rabbit in this manner, with three on the left and three on the right side of the animal. At completion of the implant procedure, the skin incision was closed with #2 sutures, topical antibiotic applied to the incision, and the animal returned to its cage. All animals with the exception of the 2 week interval were given an intramuscular dose of antibiotics and the incision site wrapped to prevent the animal's access to the wound.

C. Sample Removal and Recovery

Following the selected intervals, the rabbits were sacrificed and the back of the animal clipped. A longitudinal cut was made down the length of the spinal cord and implantation sites located. Each sample was removed from the implant pocket and transferred to an appropriately labeled vial filled with 20 ml of distilled water. The samples were then rinsed free of any gross tissue adherence and dried in a vacuum oven at room temperature for 48 hours. The dried samples were characterized for physical and mechanical property.

Tensile strength is a measure of the force, generally given in pounds per square inch (psi) for rods and pounds for tubing, required to break a polymer. Elongation is a measure of the ability of a polymer to stretch without breaking, and is generally reported as a percentage of an initial value. The term modulus defines the force, in psi or pounds, required to stretch a polymer to a given percentage of elongation.

The tensile, elongation and modulus of the polyurethane of the invention was measured by ASTM procedure D638 modified for study of rods and tubing using an Instron Universal Testing Instrument, Model 1122. The data for rods is given in Table III, and data for tubing is given in Table IV.

TABLE III

| INTERVAL | POLYMER | TENSILE (psi) | TENSILE IMPLANT 5% MOD. (pounds) | 25% MOD. | 100% MOD. | 200% MOD. | ELONG. % |
|---|---|---|---|---|---|---|---|
| 0 week | Control | 2389 | 8 | 94 | 266 | 344 | 869 |
| 4 week | | 2476 | 8 | 95 | 266 | 372 | 865 |
| 12 week | | 1979 | 10 | 98 | 254 | 327 | 848 |
| 0 week | Example I | 4414 | 7 | 118 | 311 | 430 | 404 |
| 4 week | | 5555 | 8 | 166 | 395 | 564 | 407 |
| 12 week | | 5176 | 9 | 146 | 371 | 526 | 417 |

TABLE IV

| INTERVAL | POLYMER | TENSILE (psi) | TUBING IMPLANT 5% MOD. (pounds) | 25% MOD. | 50% MOD. | 100% MOD. | ELONG. % |
|---|---|---|---|---|---|---|---|
| 0 weet | Control | 3.4 | 0.0 | 0.2 | 0.4 | 0.5 | 1073 |
| 2 WEEK | | 2.0 | 0.0 | 0.2 | 0.3 | 0.5 | 807 |
| 4 week | | 2.0 | 0.0 | 0.2 | 0.3 | 0.5 | 787 |
| 8 week | | 1.7 | 0.0 | 0.2 | 0.3 | 0.5 | 817 |
| 12 week | | 1.8 | 0.0 | 0.2 | 0.3 | 0.4 | 865 |
| 0 week | Laminate | 3.4 | 0.5 | 0.9 | 0.9 | 1.1 | 343 |
| 2 week | | 3.9 | 0.5 | 1.7 | 2.1 | 2.5 | 217 |
| 4 week | | 4.1 | 1.2 | 2.5 | 2.8 | 3.2 | 182 |
| 8 week | | 3.6 | 1.2 | 2.7 | 3.1 | 3.0 | 130 |
| 12 week | | 3.9 | 0.9 | 2.4 | 2.6 | 2.9 | 168 |

It is seen that no loss of tensile strength occurred over the 12 week study of rods and tubing of the polyurethane of the invention. In contrast, the control rod having ether linkages lost 17% of its tensile strength, and the control tubing lost 47% of its tensile strength while modulus and elongation remain substantially unchanged.

What is claimed is:

1. A thermoplastic substantially hydrophobic polyurethane comprising the reaction product of an isocyanate fraction, a diol chain extender and a hydroxy-terminated prepolymer, said isocyanate fraction comprising an aromatic diisocyanate and a first aliphatic diisocyanate, said prepolymer comprising the reaction product of a second aliphatic diisocyanate and an N-alkyldialkanolamine.

2. The polyurethane of claim 1 wherein said aromatic diisocyanate is selected from the group consisting of toluene diisocyanate, 4,4'-diphenylmethanediisocyanate, 3,3'-diphenylmethanediisocyanate, 1,4-phenylenediisocyanate, 2,2'-dimethyl-4,4'-biphenyldiisocyanate and 3,3'-dimethyl-4,4'-biphenyldiisocyanate.

3. The polyurethane of claim 1 wherein said first and second aliphatic diisocyanates have about 4 to 18 carbon atoms and are the same or different.

4. The polyurethane of claim 3 wherein said aliphatic diisocyanates are selected from the group consisting of 1,12-dodecanediisocyanate, 1,11-undecanediisocyanate, 1,10-decanediisocyanate, 1,9-nonanediisocyanate, 1,8-octanediisocyanate, 1,7-heptanediisocyanate, 1,6-hexanediisocyanate and trimethyl 1,6-hexanediisocyanate.

5. The polyurethane of claim 1 wherein said chain extender is selected from the group consisting of ethylene glycol; diethylene glycol; triethylene glycol; 1,2-propanediol; 1,3-propanediol; 1,6-hexanediol; 1,4-hydroxymethyl cyclohexane, hydroquinone dihydroxyethyl ether, and 1,4-butanediol.

6. The polyurethane of claim 1 wherein said N-alkyldialkanolamine is selected from the group consisting of diethylaminopropyldipropanolamine and dimethylaminopropyldiisopropanolamine.

7. A thermoplastic substantially hydrophobic polyurethane comprising the reaction product of an isocyanate fraction, a chain extender, and a hydroxy-terminated prepolymer, said isocyanate fraction comprising a mixture of an aromatic diisocyanate and a nonaromatic diisocyanate, said prepolymer comprising the reaction product of an aliphatic diisocyanate and a bis(hydroxyalkyl) tertiary amine.

8. The polyurethane of claim 7 wherein said bis (hydroxyalkyl) tertiary amine is selected from the group having the formula

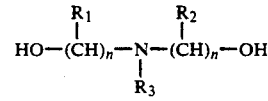

wherein $R_1$ and $R_2$ are independently hydrogen or lower alkyl, $R_3$ is selected from the group consisting of lower alkyl or dialkylaminoalkylene, n is 2 to 6, alkyl is 1 to about 18 carbon atoms and alkylene is 2 to about 6 carbons atoms.

9. A thermoplastic substantially hydrophobic polyurethane comprising the reaction product of an isocyanate fraction, 1,4-butanediol and a hydroxy-terminated prepolymer, said isocyanate fraction comprising 4,4-diphenylmethanediisocyanate and 1,6-hexanediisocyanate, said prepolymer comprising the reaction product of 1,6-hexanediisocyanate and N-butyldiethanolamine.

10. An antithrombogenic polyurethane comprising the reaction product of an isocyanate fraction, a diol chain extender and a hydroxy-terminated prepolymer, said isocyanate fraction comprising an aromatic diisocyanate and a first aliphatic diisocyanate, said prepolymer comprising the reaction product of a second aliphatic diisocyanate and an N-alkyldialkanolamine, said amine being protonated and complexed with heparin.

11. The polyurethane of claim 10 wherein said aromatic diisocyanate is selected from the group consisting of toluene diisocyanate, 4,4'-diphenylmethanediisocyanate, 3,3'-diphenylmethanediisocyanate, 1,4-phenylenediisocyanate, 2,2'-dimethyl 4,4'-biphenyldiisocyanate and 3,3'-dimethyl-4,4'-biphenyldiisocyanate.

12. The polyurethane of claim 10 wherein said first and second aliphatic diisocyanates have about 4 to 18 carbon atoms and are the same or different.

13. The polyurethane of claim 12 wherein said aliphatic diisocyanates are selected from the group consisting of 1,12-dodecanediisocyanate, 1,11-undecanediisocyanate, 1,10-decanediisocyanate, 1,9-nonanediisocyanate, 1,8-octanediisocyanate, 1,7-heptanediisocyanate, 1,6-hexanediisocyanate and trimethyl-1,6-hexanediisocyanate.

14. The polyurethane of claim 10 wherein said chain extender is selected from the group consisting of ethylene glycol; diethylene glycol; triethylene glycol; 1,2-propanediol; 1,3-propanediol; 1,6-hexanediol; 1,4-hydroxymethyl cyclohexane, hydroquinone dihydroxyethyl ether, and 1,4-butanediol.

15. The polyurethane of claim 10 wherein said N-alkyldialkanolamine is selected from the group consisting of N-methyldiethanolamine, N-butyldiethanolamine, N-dodecyldiethanolamine, N-ethyldiisopropanolamine and N-octadecyldiethanolamine.

16. The polyurethane of claim 10 in the form of a rod.

17. The polyurethane of claim 10 in the form of a tubing.

18. A bioactive polyurethane comprising the reaction product of an isocyanate fraction, a chain extender, and a hydroxy terminated prepolymer, said isocyanate fraction comprising a mixture of an aromatic diisocyanate and a nonaromatic diisocyanate, said prepolymer comprising the reaction product of an aliphatic diisocyanate and a bis(hydroxyalkyl) tertiary amine, said amine being protonated and complexed with a heparin.

19. The polyurethane of claim 18 wherein said bis(hydroxyalkyl) tertiary amine is selected from the group having the formula

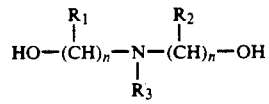

wherein R and $R_2$ are independently hydrogen or lower alkyl, $R_3$ is selected from the group consisting of lower alkyl or dialkylaminoalkylene, n is 2 to 6, alkyl is 1 to about 18 carbon atoms and alkylene is 2 to about 6 carbons atoms.

20. An antithrombogenic polyurethane comprising the reaction product of an isocyanate fraction, 1,4-butanediol and a hydroxy-terminated prepolymer, said isocyanate fraction comprising 4,4'-diphenylmethanediisocyanate and 1,6-hexanediisocyanate, said prepolymer comprising the reaction product of 1,6-hexanediisocyanate and N-butyldiethanolamine said amine being protonated and complexed with heparin.

* * * * *